United States Patent
Wang et al.

(10) Patent No.: US 9,581,314 B2
(45) Date of Patent: Feb. 28, 2017

(54) INTEGRATING CONE FOR AN ILLUMINATION DEVICE

(71) Applicant: Excelitas Canada, Inc., Vaudreuil-Dorion (CA)

(72) Inventors: Yong Wang, Markham (CA); Paul Constantinou, Burlington (CA); Sola Kuk, Toronto (CA)

(73) Assignee: Excelites Canada, Inc., Voudreuil-Doxion (CA)

( * ) Notice: Subject to any disclaimer, the term of this patent is extended or adjusted under 35 U.S.C. 154(b) by 94 days.

(21) Appl. No.: 14/691,987

(22) Filed: Apr. 21, 2015

(65) Prior Publication Data
US 2016/0312980 A1    Oct. 27, 2016

(51) Int. Cl.
| | | |
|---|---|---|
| F21V 13/08 | (2006.01) |
| F21K 99/00 | (2016.01) |
| G01N 21/64 | (2006.01) |
| G02B 17/00 | (2006.01) |
| G02B 27/09 | (2006.01) |
| G02B 19/00 | (2006.01) |

(Continued)

(52) U.S. Cl.
CPC .............. *F21V 13/08* (2013.01); *F21K 9/52* (2013.01); *G01N 21/6458* (2013.01); *G02B 17/004* (2013.01); *G02B 19/0061* (2013.01); *G02B 27/0994* (2013.01); *F21Y 2101/02* (2013.01); *F21Y 2101/025* (2013.01); *F21Y 2113/005* (2013.01); *G01N 2021/6471* (2013.01); *G01N 2021/6478* (2013.01)

(58) Field of Classification Search
CPC .......... F21V 13/08; F21V 5/008; F21V 13/00; F21V 13/02; F21V 13/12; F21V 99/00; F21K 9/52; G01N 21/6458; G01N 2021/6471; G01N 2021/6478; G02B 17/004; G02B 19/0061; G02B 27/0994; G02B 19/00; G02B 19/0023; G02B 19/0047; G02B 19/0052; G02B 21/00; G02B 21/08; G02B 21/082; F21Y 2101/02; F21Y 2101/025; F21Y 2113/005
See application file for complete search history.

(56) References Cited

U.S. PATENT DOCUMENTS

| | | | |
|---|---|---|---|
| 7,898,665 B2 | 3/2011 | Brukilacchio et al. | |
| 8,998,435 B2 * | 4/2015 | Brick | G02B 6/0028 353/20 |
| 9,250,431 B2 * | 2/2016 | Wang | G02B 21/08 |

(Continued)

FOREIGN PATENT DOCUMENTS

WO    2007146373 A2    12/2007

*Primary Examiner* — Bao Q Truong
(74) *Attorney, Agent, or Firm* — Peter A. Nieves; Sheehan Phinney Bass & Green PA (57) ABSTRACT

A device for increasing the optical power of a solid state light source in the green and/or yellow bands, is disclosed. The device has an integral body having an ingress surface configured to receive light from an emitting portion of the solid state light source, an egress surface substantially opposite the ingress surface, and a recess formed within the body. The recess has an input opening in the ingress surface, an output opening in the egress surface, and a recess surface within the body extending between the input opening and the output opening. The recess surface is configured to reflect visible light with Lambertian scatter characteristics.

21 Claims, 8 Drawing Sheets

(51) Int. Cl.
*F21Y 101/02* (2006.01)
*F21Y 113/00* (2016.01)

(56) References Cited

U.S. PATENT DOCUMENTS

| | | |
|---|---|---|
| 2004/0012864 A1 | 1/2004 | Mima |
| 2013/0058114 A1 | 3/2013 | Reiners |
| 2013/0314893 A1 | 11/2013 | Paquette |
| 2014/0016297 A1 | 1/2014 | Mehl |
| 2014/0160782 A1* | 6/2014 | Harada ................ F21S 48/1145 362/538 |
| 2014/0340869 A1 | 11/2014 | Wang et al. |
| 2015/0077972 A1* | 3/2015 | Sugiyama ............ G02B 6/0005 362/84 |

* cited by examiner

INTEGRATING CONE FOR AN ILLUMINATION DEVICE

FIELD OF THE INVENTION

The present invention relates to illumination, and more particularly, is related to solid state illumination devices.

BACKGROUND OF THE INVENTION

Solid state technology has progressed very far in recent decades. However there is still significant room for improvement in the green/yellow/amber range of the electromagnetic spectrum, approximately 520-600 nm. Direct light emitting diodes (LEDs) or laser diodes in this range are traditionally very low powered and/or inefficient from an electro-optical perspective. This issue with solid state lighting producing light at wavelengths in the green/yellow/amber range is fundamentally limited by the physics of the semiconductor materials used in the construction of these devices, as the band-gap of the materials does not favor emission of light in this spectral range. This problem is commonly referred to in the industry as the 'green gap'.

Solid state lighting solutions are sought after in all areas of general lighting to improve energy efficiency and increase luminaire lifetime. However, existing solid state apparatuses and methods for generating green light that meets optical power requirements for fluorescence imaging applications are generally costly. The conventional approach has been either devices having low output in the green-yellow band or low coupling efficiency for large area LEDs. LED array or laser pumped crystal or phosphor solutions are relatively expensive compared to arc lamps for some applications with low cost requirements.

A conventional approach to producing broadband light, such as white, is to use ultra violet light, royal blue, or near-ultra violet light from LEDs which have a phosphor powder deposited onto the LED surface. The most popular of these methods is creation of a 'white' LED which includes a phosphor of Ce:YAG (cerium doped yttrium aluminum garnet, $Y_3Al_5O_{12}:Ce_{3+}$) suspended in an encapsulating material such as silicone, embedded in a transmissive ceramic, or deposited directly onto a blue LED die or die array with a peak wavelength between about 445 nm and 475 nm. The light absorbed by the phosphor is converted to a broadband green/yellow/amber light, which combines with un-absorbed scattered blue light to produce a spectrum that appears white. The brightness of white light is limited by the blue light intensity from the LED, phosphor quantum efficiency, and thermal quenching, especially in the yellow (approximately 560 nm) and amber (approximately 590 nm) spectral bands. Higher power LEDs are available, but the increase in power scales with an increase in the LED emitting area. The coupling efficiency from the illumination source (LED surface) to the objective plane of a microscope objective is inversely proportional to the source size at the same light intensity. Thus, the power delivered to the microscope objective plane cannot typically be increased by simply increasing the LED surface area (it is an Etendue limited optical system).

Another way to achieve bright yellow and amber light is using single crystal Ce:YAG LED pumped by an LED array. The efficiency of such a device is limited by the total internal reflection of such a luminescent material due to its high index of refraction, and more importantly, coupling from LED to crystal. This results in a need of a large number of LEDs to achieve the brightness needed, which increases cost, size, and thermal/electrical requirements on systems employing this method. For example, see U.S. patent Ser. No. 12/187,356.

A third way of generating high powers of light in the green gap consists of using Ce:YAG in crystal form and pumping this structure with a blue (approximately 440-490 nm) laser from the front or back of the crystal. For example, U.S. patent application Ser. No. 13/900,089 describes an optical system using this concept and the predicted improvement in electro-optical coupling efficiency to the focal plane of a microscope has been validated. This approach is very effective in producing a scalable amount of power in the green/yellow band but can be costly. The particular shape and size of the crystal, multiple laser diodes, and cooling methods lead to increased assembly and manufacturing costs.

Other combinations of lasers and phosphors have also been suggested for many high brightness applications including fluorescence illumination, such as U.S. patent application Ser. No. 13/897,237, and other applications such as automotive headlights, for example, U.S. patent application Ser. No. 13/697,782, and digital projection systems, such as U.S. patent application Ser. No. 13/942,603, but these methods are still unable to meet the same cost targets as mercury or xenon arc lamps, which are currently the industry standard. Therefore, there is a need in the industry to address one or more of the above mentioned shortcomings.

SUMMARY OF THE INVENTION

Embodiments of the present invention provide an integrating cone for an illumination device. Briefly described, the present invention is directed to a device for increasing the optical power and coupling efficiency of a solid state light source in the green and/or yellow bands. The device has an integral body having an ingress surface configured to receive light from an emitting portion of the solid state light source, an egress surface substantially opposite the ingress surface, and a recess formed within the body. The recess has an input opening in the ingress surface, an output opening in the egress surface, and a recess surface within the body extending between the input opening and the output opening. The recess surface is configured to reflect visible light with Lambertian scatter characteristics.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

DETAILED DESCRIPTION

The following definitions are useful for interpreting terms applied to features of the embodiments disclosed herein, and are meant only to define elements within the disclosure. No limitations on terms used within the claims are intended, or should be derived, thereby. Terms used within the appended claims should only be limited by their customary meaning within the applicable arts.

As used within this disclosure, "cone" refers to an inset surface having generally conically shaped profile. The terms cone and conical may refer to sections of a cone, for example, a cone omitting the apex. Some variations to a purely conical shape are also considered to be described with these terms, as described further below. The term "cone cavity" refers to a device having a cone shaped cavity formed therein.

As used within this disclosure, "substantially" means "very nearly," or within expected manufacturing tolerances. For example, substantially parallel surfaces refer to surfaces that are parallel within any manufacturing tolerance expected by a person having ordinary skill in the art.

As used within this disclosure, "Lambertian scatter properties/characteristics" refers to Lambertian reflectance, a property that defines an ideal "matte" or diffusely reflecting surface. The apparent brightness of such a surface to an observer is the same regardless of the observer's angle of view. In particular, the surface's luminance is isotropic, and the luminous intensity substantially obeys Lambert's cosine law.

Reference will now be made in detail to embodiments of the present invention, examples of which are illustrated in the accompanying drawings. Wherever possible, the same reference numbers are used in the drawings and the description to refer to the same or like parts.

Exemplary embodiments of the present invention disclose a system, device and method for increasing the optical power in the green band and coupling efficiency to a microscope using low cost solid state LED components combined with an integrating cone. The embodiments increase the total power in the green band but also improve the coupling efficiency to a microscope objective plane.

Generally, as described previously, the output intensity of an LED is limited by the maximum LED driving current density. Increasing the LED area can increase total optical power from the LED. But the optical output at an objective plane is not proportional with the LED area increasing. Most optical power increasing by increasing the LED area is stopped by the aperture inside the microscope. The present embodiments use a cone component to increase coupling efficiency from a large area LED to an objective plane of the microscopy system.

There is competition to provide a basic solid state lighting (SSL) illumination system, and many systems on the market today still do not offer the performance of the traditional arc lamp systems. The first embodiment, described below, approaches an arc lamp system, such as the X-Cite 120 for example, in terms of performance and cost.

Figure 1:
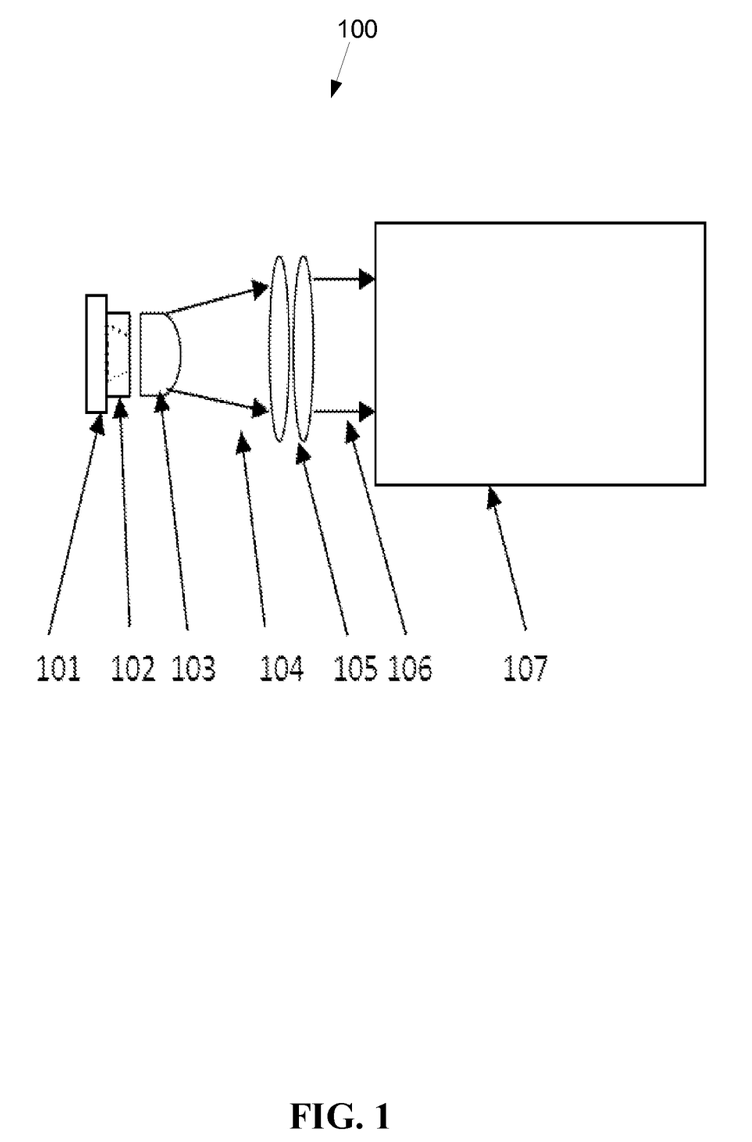
FIG. 1 is a schematic diagram of a first exemplary embodiment of an illumination system with increased optical power in the green band.

FIG. 1 is a schematic diagram of a first embodiment of an illumination system 100 with increased optical power in the green band. The overall optical layout is generally typical for a microscopy illumination system, however, as described below, the first embodiment includes features not present in previous systems.

A conventional large area white LED 101, for example, having an emitting area greater than 9 mm$^2$, is low cost and may utilize a phosphor layer deposited on a blue or UV LED to create a broadband white light spectrum, for example, Luminius CBT-140. Although the power output of such a large LED 101 is relatively high compared to a more standard 1 mm$^2$ LED, the coupling efficiency in prior art systems to a microscope 107 is relatively poor. Under the first embodiment, the output of the LED 101 is integrated and reshaped by a cone cavity 102. The cone cavity 102 has high reflectivity and Lambertian scattering properties. The dimensions and shape of the cone cavity 102 transfer an input beam, namely the light emitted from the large area LED 101, to an output beam emitting from the cone cavity 102, as described further below. The output beam has a smaller diameter than the input beam, improving the coupling efficiency to a microscope 107. The output beam of the cone cavity 102 is collected by a lens 103. For example, the lens 103 may be made from BK7 material, and be a ½ ball lens with a diameter of 10 mm (radius of 5 mm). A lens output beam 104 emitting from the lens 103 may be collimated by a collimating lens 105, and collimated light 106 output by the collimating lens 105 may be coupled to the microscope 107.

Figure 2:
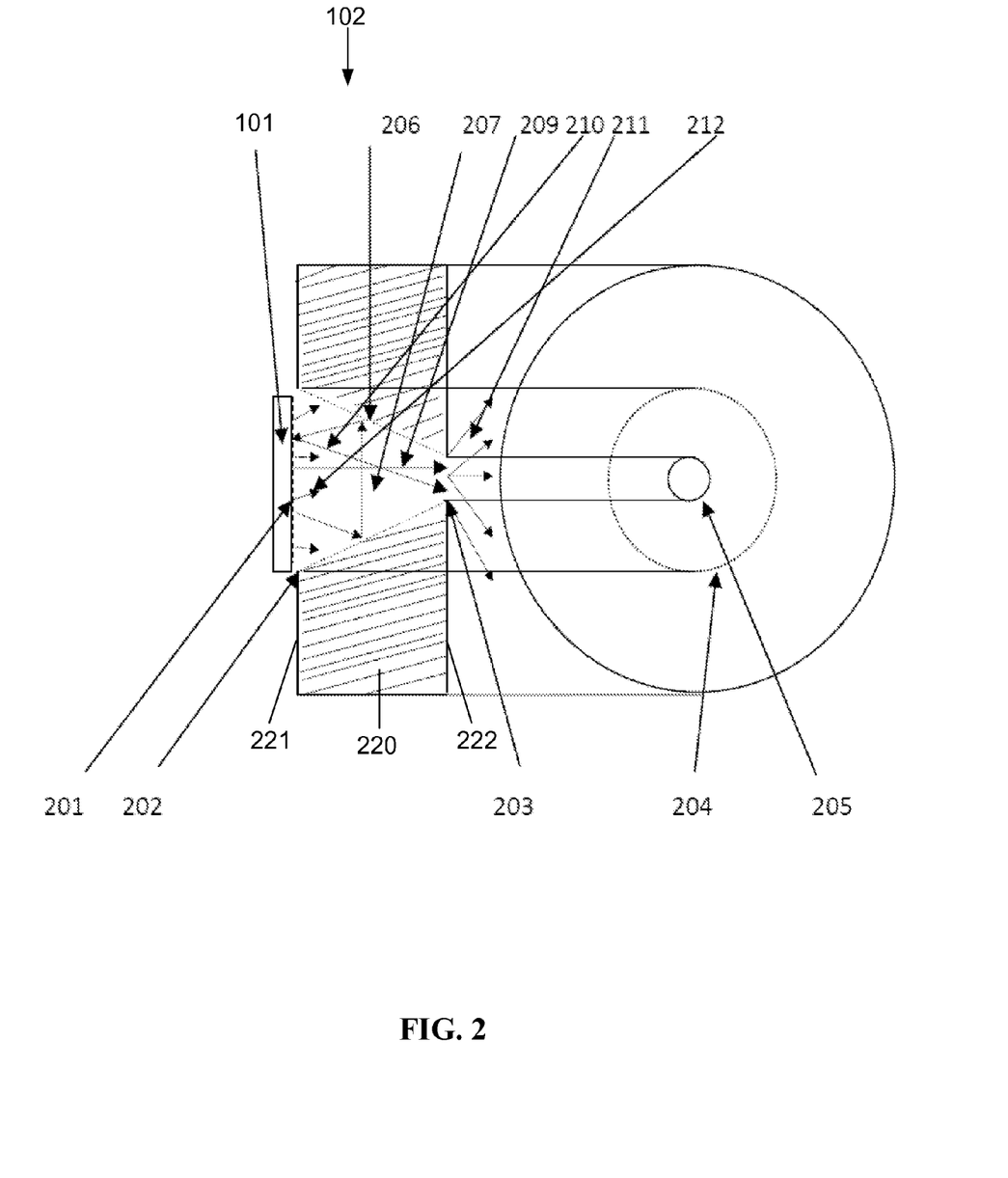
FIG. 2 is a schematic diagram showing a side view of the detail structure of a cone cavity of the cone device of the system of FIG. 1, shown beside a front view scale.

FIG. 2 shows a side view of the detail structure of the cone cavity 102 beside a bulls-eye scale shown from a front view. The cone cavity 102 includes an integral body 220 formed of a rigid material, with an ingress side 221 and an egress side 222 opposite the ingress side 221. The cone cavity 102 may be formed as an aperture, or cavity 207, in the body 220, extending from the ingress side 221 to the egress side 222. The input opening 202 of the cone cavity 102 is formed in the ingress side 221 of the body 220, and has similar size to the emitting area of the large LED 101, for example, greater than 9 mm$^2$. The input opening 202 of the cone cavity 102 may be round 204 as shown in FIG. 2, such as a Luminus Devices CBT-140, or square (not shown), such as a Luminus Devices CBT-90.

An output opening 203 of the cavity 207 is formed in the egress side 222 of the body 220. The output opening 203 may be round 205 or square, corresponding to the shape of input opening 202. Other shapes of the input opening 202 and output opening 203 are possible, for example, such that the shape of the input opening 202 corresponds to the shape of the emitting area of the large LED 101. For example a cone may correspond to a round LED, while a pyramidal shape may correspond for square, or rectangular LEDs. By extension, for any shaped LED, the cone would preferably mimic the geometric shape the LED is based on. The input opening 202 and the output opening 203 may have different shapes. Typically, the output shape is circular since this corresponds to the typical aperture stop geometry in a microscope optical train. In general the cone geometry will preferably match the LED source shape on the input side 202, and be matched the aperture stop geometry in a microscope 107 (FIG. 1) on the output side 203.

The diameter of the output opening 203 is a smaller than the input opening 202, for example the output to input area ratio may generally be in range of 1.5 to 10 times depending on applications, but not limited to this range. While several exemplary dimensions are provided herein, a person having ordinary skill in the art will recognize the dimensions and ratio of the output opening to the input opening will depend on several factors, for example, the LED 101 size and coupling requirements to the microscope 107 (FIG. 1).

The material used for the cone cavity 102 may generally be any suitable base material and a scattering coating applied to it. Alternatively, the cone cavity 102 may be molded as an integral part from the scattering material. For example, scattering materials with the desirable optical properties includes Spectraflect and/or Spectralon from Labsphere. Such materials may be coated or molded, and have a typical reflectance of 0.99 within 400-700 nm. The internal surface 206 of the cavity 207 is highly reflective, for example, where the reflectivity is preferably higher than 99% and with Lambertian scatter characteristics. The internal surface 206 in the first embodiment may be reflective to light in the visible spectrum. However, alternative embodiments using a similar process/methodology may have a UV LED with a phosphor coating, effectively extending the reflectivity requirement more generally to include UV to near IR (eg, 350-800 nm).

Under the first embodiment, the cavity 207 is generally conically shaped, where the input opening 202 and output opening 203 are substantially concentric, with centers of openings 202, 203 sharing a common axis of the cavity 207. The profile of a cutaway of the internal surface 206 may generally be formed from straight lines, but other embodiments may employ a curved surface with respect to the center axis of the cavity 207, for example, a convex curved surface, or a concave profile curved surface. Other curves are also possible, for example, a cavity an elliptical or parabolic profile.

The cone cavity 102 with Lambertian scatter characteristics and high reflectivity of the internal surface 206 combined with the highly reflective LED surface (due to the high index refractivity of the LED substrate) act as integrating sphere. Multiple reflections of the light emitted from the LED 101 occur in the cavity 207. An exemplary material used for the body 220 forming the cavity 207 is Spectralon from LabSphere. The internal reflectivity of the cone cavity 102 is greater than 99% and with Lambertian scattering characteristics. For example, using a Luminous CBT-140 the input diameter of the cone 202 may be 4.5 mm, and the exit diameter of the cone 203 may be 1.8 mm.

The green or yellow light beam 212 emitted from a phosphor layer 201 on the LED directly exits 209 the cone cavity 102 or indirectly exits though multiple reflections 211 in the integrating cavity. The output beam 203 from cone cavity 102 is smaller in size compared with the yellow/green beam 212. Similarly, a portion of the blue light directly exits the cone 203, but most of the blue light from the large area LED 101 is reflected from cavity surface 207 back to the phosphor layer 201, thus generating more light in the yellow and green band than is produced by light directly emitted by the LED 101, which only interacts with the phosphor layer once. The blue light is therefore recycled, and at the output opening 203 of the cone cavity 102 the ratio of green to blue light is increased. The combination of smaller source size at the output opening 203 and increased light in the green band significantly improves the green light coupled to the objective plane of the microscope 107 (FIG. 1) and allows for improved fluorescence imaging. It is desirable to have equal brightness in all wavelength bands and the white LED 101 alone has insufficient light in the green and yellow bands.

Figure 3A:
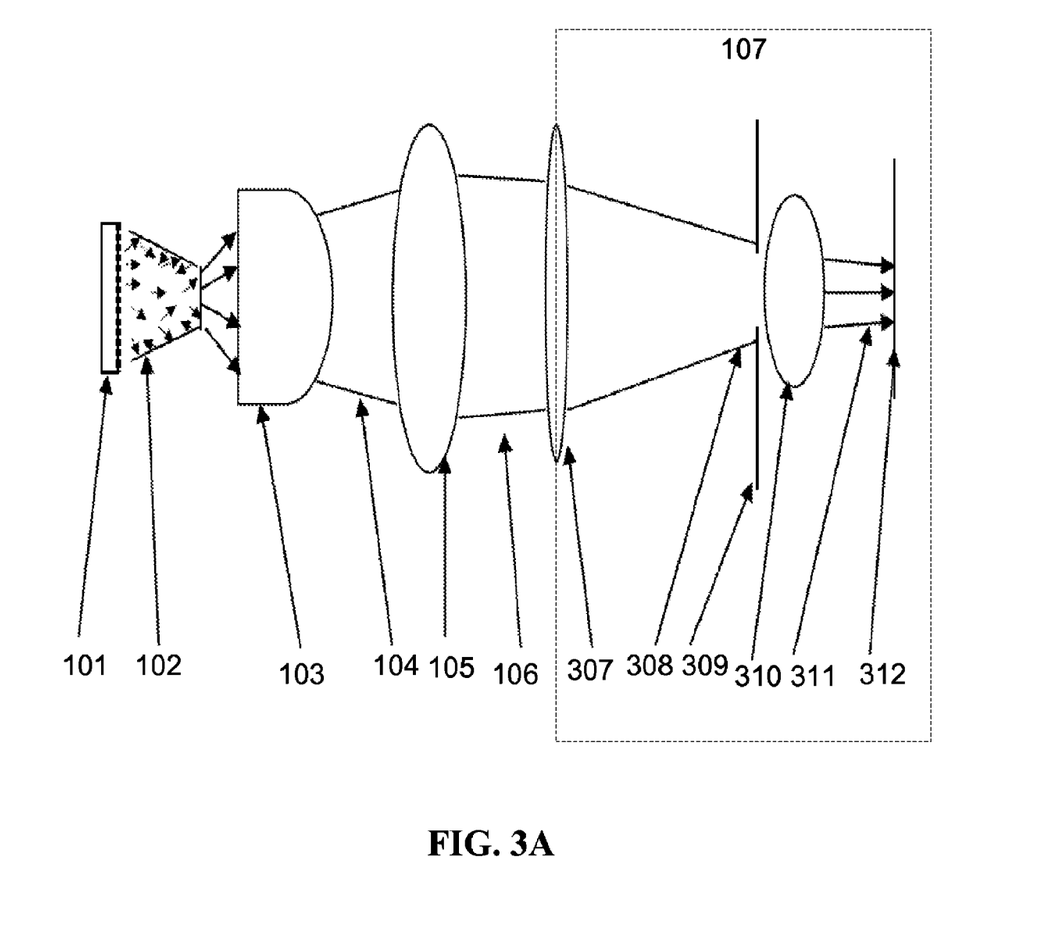
FIG. 3A is a schematic diagram showing the light throughput of the first embodiment of an illumination system.

FIG. 3A shows a diagram of a fluorescence microscope illumination system with the cone cavity 102 to boost light output to the microscope 107. The LED 101 may be, for example, a large area low cost white LED or a lime LED. The output of LED 101 is integrated and reshaped by the cone cavity 102 which has high reflectivity and Lambertian scattering characteristics as described above. The output from the cone cavity 102 is collected by the lens 103. The lens output beam 104 is collimated by collimating lens 105. The collimated light 106 is coupled to a microscope relay lens 307. A partial beam 308 from lens 307 is directed toward an aperture 309, where most of the beam 308 passes through the aperture 309 and becomes the input to an objective lens 310. The output beam 311 is directed to an objective plane 312.

Figure 3B:
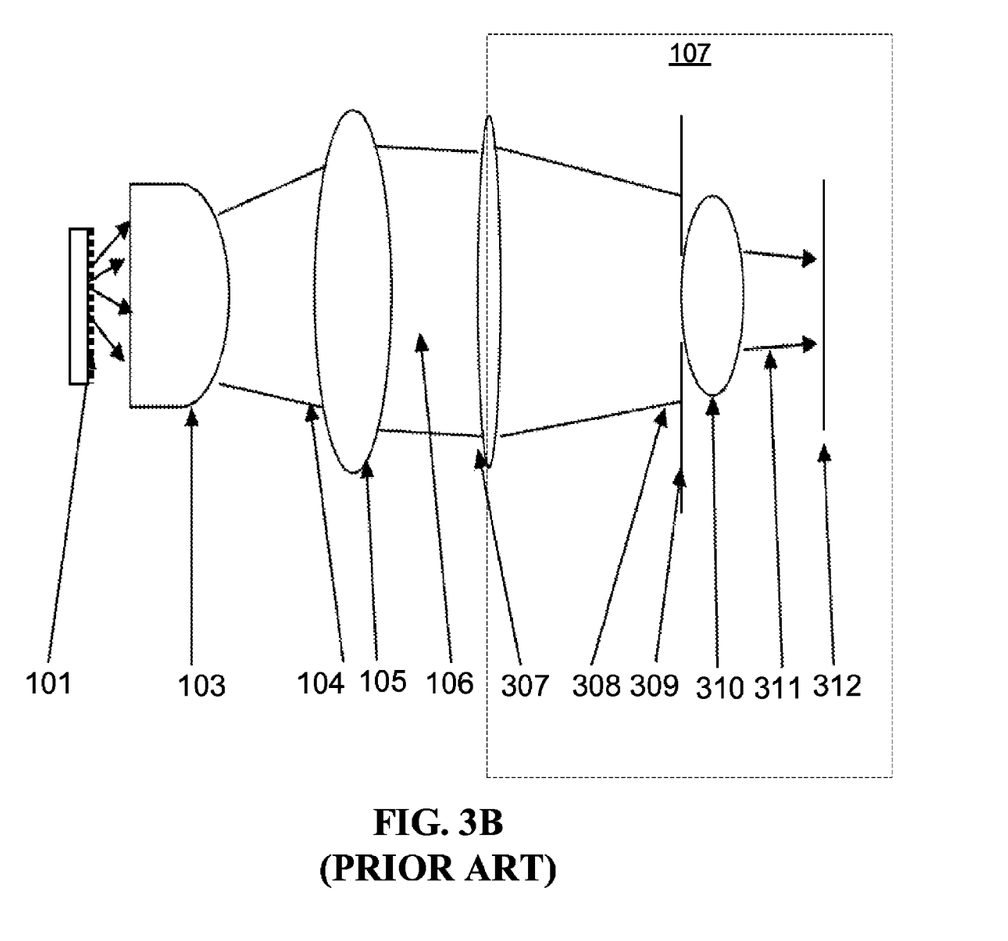
FIG. 3B is a schematic diagram of the light throughput of a prior art illumination system.

FIG. 3B is a schematic diagram of the light throughput of a prior art illumination device, which is similar to FIG. 3A, but omits the cone cavity 102. As shown by FIG. 3A, the small size of the source beam emitted from the cone cavity 102 results in a small beam size 308. In contrast the beam size of the 308 of FIG. 3B is much larger than the beam size 308 of FIG. 3A, resulting in the aperture 309 of FIG. 3B blocking much more light than the aperture 309 of FIG. 3A. In FIG. 3A, more light from the illuminator with the cone cavity 102 reaches to objective plane 312 than the prior art illuminator of FIG. 3B without the cone cavity 102.

Figure 4:
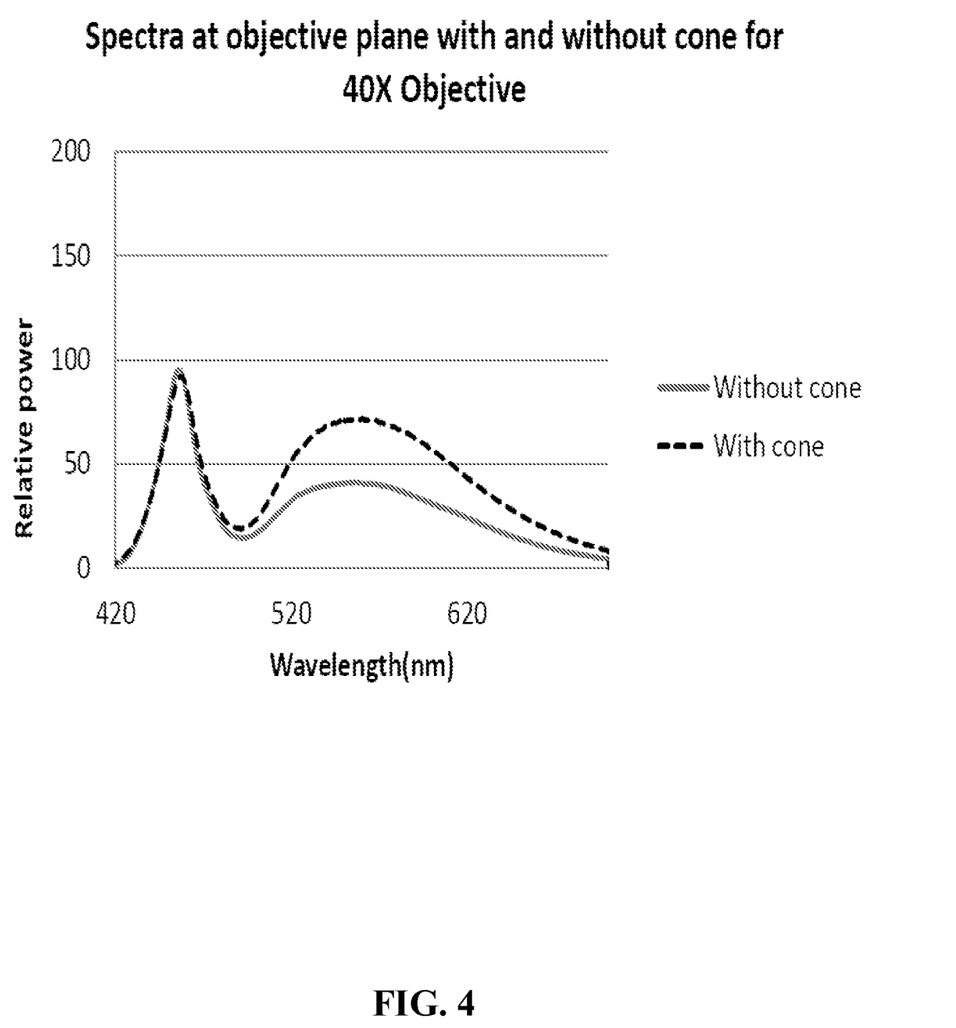
FIG. 4 is a plot comparing the relative power output of the optical systems of FIG. 3A and FIG. 3B.

Experimental results are consistent with the above description. An experiment was conducted using a luminous round CBT-140 LED with a 4.25 mm diameter, a cone cavity 102 with reflectivity greater than 99% and Lambertian scattering characteristics. The diameter of the cone input opening 202 (FIG. 2) was 4.5 mm, and the diameter of output opening 203 (FIG. 2) of the cone cavity 102 (FIG. 2) was 1.8 mm. The microscope was a Zeiss axio-observer A1 with objectives: 10×/NA0.25, 20×/NA0.8, and 40×/0.75. FIG. 4 shows a spectral comparison 40× objective plane between the same illuminator with and without the cone cavity 102. The spectra in the 500-700 nm range is clearly improved with the cone cavity 102.

Table 1 shows the optical output power comparison between illumination paths with and without a cone cavity for same LED.

TABLE 1

|  | Peak wavelength/ band width | 10x/ NA: 0.25 | 20x/ NA: 0.8 | 40x/ NA: 0.75 |
| --- | --- | --- | --- | --- |
| With Cone | 545 nm/25 nm | 43 | 81 | 33 |
|  | 562 nm/40 nm | 77 | 146 | 59 |
|  | 470 nm/40 nm | 40 | 79 | 29 |
|  | 628 nm/40 nm | 55 | 109 | 44 |
| Without Cone | 545 nm/25 nm | 28 | 68 | 19 |
|  | 562 nm/40 nm | 50 | 121 | 34 |
|  | 470 nm/40 nm | 40 | 95 | 26 |
|  | 628 nm/40 nm | 34 | 85 | 24 |
| Improvement | 545 nm/25 nm | 50% | 19% | 74% |
|  | 562 nm/40 nm | 53% | 21% | 75% |
|  | 470 nm/40 nm | −1% | −17% | 11% |
|  | 628 nm/40 nm | 62% | 28% | 85% |

As seen by the data in Table 1, the optical power at objective plane of a microscope was improved from 19% to 70% in the green and yellow bands depending on the microscope objective selected. Because the different objectives have different numerical aperture and input diameter, the coupling improvement is variable. For the blue band, the power at the objective plane is increased for 40× but it slight decrease for 10× and 20× because some of the blue light is reflected back onto the phosphor which increases the emission in the green and yellow bands.

Figure 5:
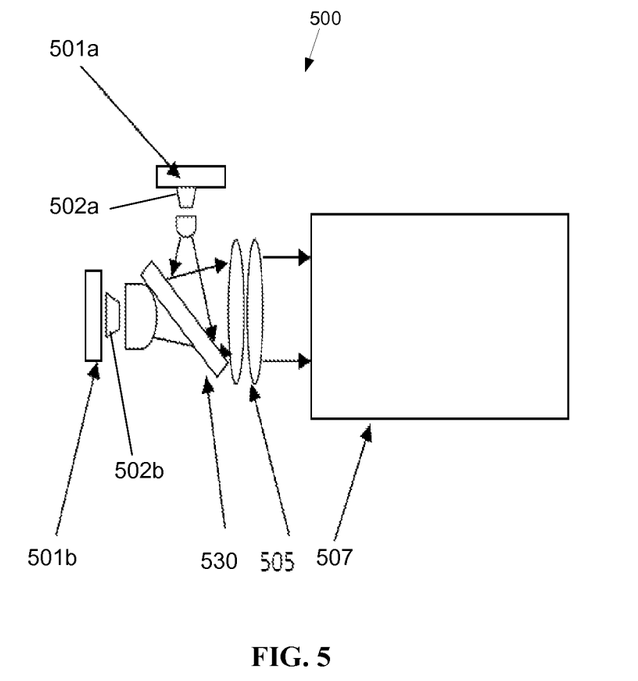
FIG. 5 is a schematic diagram of a second embodiment of an illumination system with increased optical power in the green band.

FIG. 5 is a schematic diagram of a second embodiment of an illumination system 500 with increased optical power in the green band. As shown in FIG. 5, the illumination system 500 may include multiple LED light sources 501, where integrating cones 502a, 502b may be coupled with one or more of the multiple LEDs 501a, 501b. The LEDs 501a, 501b may have different properties, for example, producing light having of different wavelengths, different beam sizes, and/or different power characteristics. The light of the LEDs 501a, 501b and integrating cones 502a, 502b may be combined by a blending means 530, for example, a prism or dichroic plates. After light of multiple LED sources 501a, 501b is combined by the blending means 530, the combined light may be collimated by a collimating lens 505. The collimated beam may be coupled to a microscopy system 507. While FIG. 5 shows two LEDs 501a, 501b and two integrating cones 502a, 502b, alternative embodiments may have two, three, or more LEDs, and two, three or more integrating cones. Furthermore, there is not necessarily a one-to-one relationship between the number of LEDs and the number of integrating cones. For example, a first LED may be coupled with an integrating cone, and a second LED may not be coupled with an integrating cone.

Figure 6:
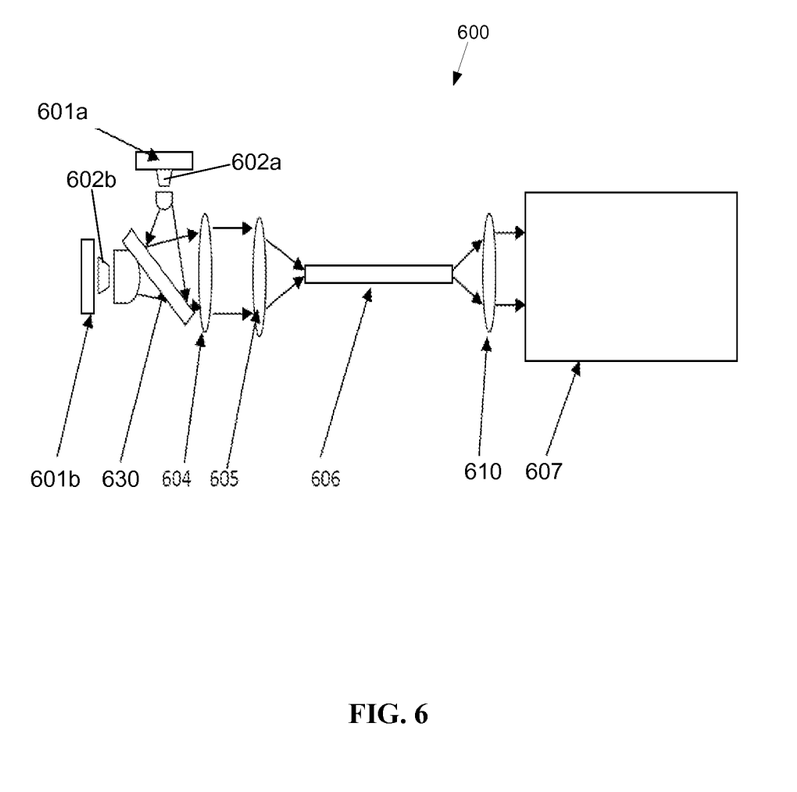
FIG. 6 is a schematic diagram of a third embodiment of an illumination system with increased optical power in the green band.

As shown in FIG. 6, under a third embodiment of an optical system 600, one or more integrating cones 602a, 602b can also be used in light guide coupled applications to increase the green optical power coupled to a light guide 606. The light of the LEDs 601a, 601b and integrating cones 602a, 602b may be combined by blending means 630. Collimated light from a collimating lens 604 is coupled to the light guide 606 by using a focus lens 605. The output of the light guide 606 may be collimated and coupled to a microscopy system 607 by an optical lens system 610. The blending means 630 may include one or more dichroic filters/plates. The blending means 630 may also blend in light from light sources in addition to or instead of LED 601a, which may or may not incorporate one or more additional integrating cones.

Figure 7:
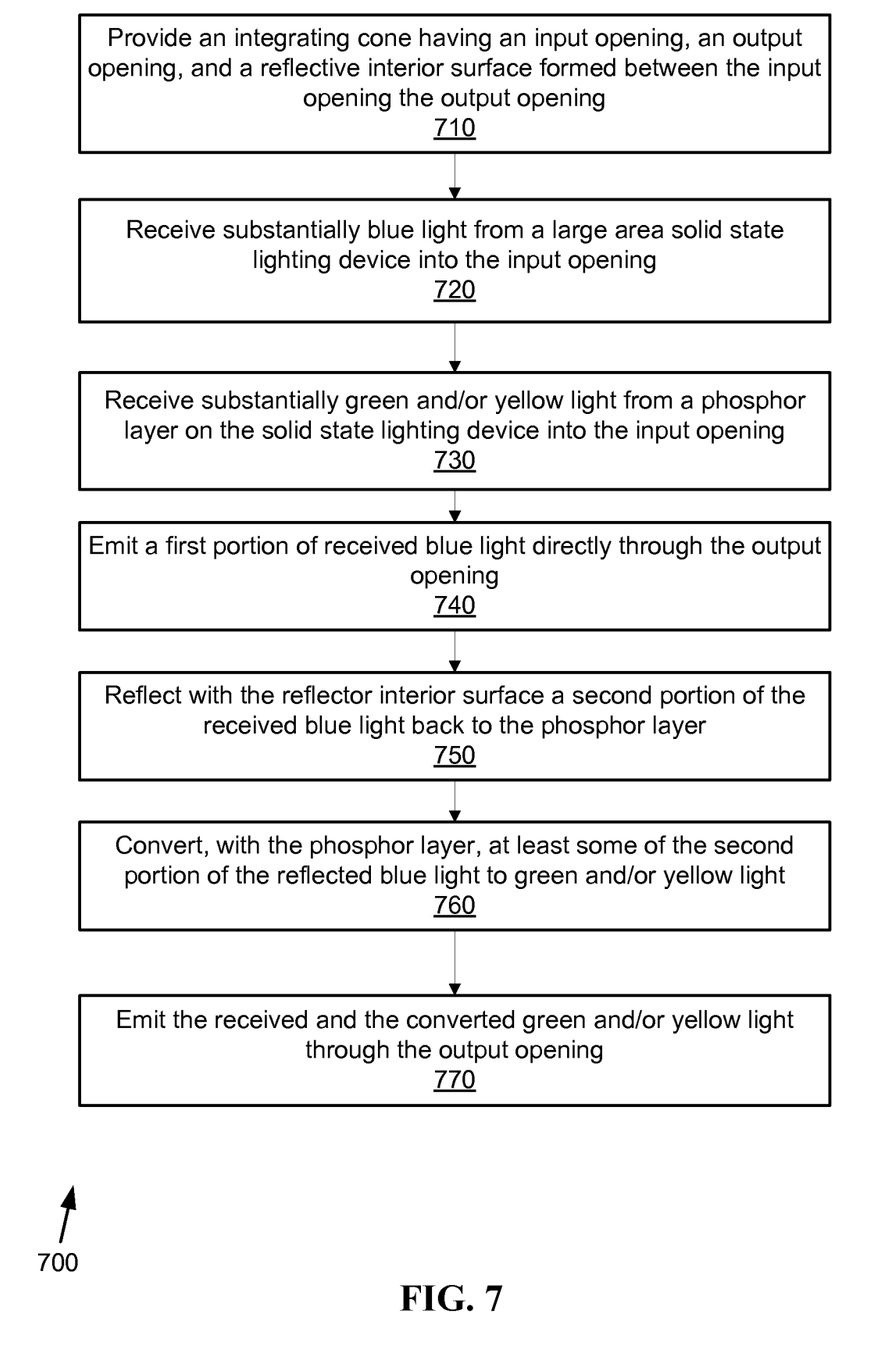
FIG. 7 is a flowchart of an exemplary method for increasing the optical power of a solid state light source with a phosphor layer in the green and/or yellow bands for improved fluorescence microscopy

FIG. 7 is a flowchart of an exemplary method 700 for increasing the optical power of a solid state light source with a phosphor layer in the green and/or yellow bands for improved fluorescence microscopy. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. The method is described with reference to FIG. 2.

An integrating cone cavity 102 having an input opening 202, an output opening 203, and a reflective interior surface 206 formed between the input opening 202 the output opening 203 is provided, as shown in block 710. Substantially blue light from a large area solid state lighting device 101 is received into the input opening 202, as shown by block 720. Substantially green and/or yellow light from a phosphor layer 201 on the solid state lighting device 101 is received into the input opening 202, as shown by block 730. A first portion of received blue light is directly emitted through the output opening 203, as shown by block 740. The reflector interior surface 206 reflects a second portion of the received blue light back to the phosphor layer 201, as shown by block 750. The phosphor layer 201 converts at least some of the second portion of the reflected blue light to green and/or yellow light as shown by block 760. The received and the converted green and/or yellow light is emitted through the output opening 203 as shown by block 770.

The embodiments described above offer a balance between cost and performance and for cost limited applications, providing a solution with increased optical power in critical wavelength bands compared to previous solutions. The embodiments can be used for directly coupled or light guide coupled illumination products where a larger LED chip is utilized in order to meet the optical power requirements of an application. The embodiments may be particularly useful in fluorescence imaging application where it is desirable to have equal power across all visible wavelength bands.

While the above embodiments have generally described an integrating cone in the context of a microscopy system, the use of the integrating cone is not limited to such applications. Persons having ordinary skill in the art will recognize the integrating cone may be used in many applications that would benefit from low cost and/or passive increase in the green/yellow/amber band.

While the above embodiments describe generate more green/yellow light, the generalized approach described above may be used to generate more light in other wavelength ranges, for example, using different colored LEDs as the primary light source, coupled with different secondary light sources providing complementary wavebands.

In summary, it will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A device for increasing the optical power of a solid state light source in the green and/or yellow bands, comprising:
    a body further comprising:
        an ingress surface configured to receive light from an emitting portion of the solid state light source;
        an egress surface substantially opposite the ingress surface; and
        a recess formed within the body, further comprising an input opening in the ingress surface, an output opening in the egress surface, and a recess surface within the body extending between the input opening and the output opening,
    wherein the recess surface is configured to reflect visible light with Lambertian scatter characteristics, a profile shape of the output opening corresponds to a profile shape of the input opening, and the size of the output opening is smaller than the input opening.

2. The device of claim 1, wherein the body is an integral body.

3. The device of claim 1, wherein the body ingress surface is substantially parallel to the body egress surface.

4. The device of claim 3, wherein the recess surface comprises a substantially conically shaped surface.

5. The device of claim 4, wherein a center axis of the conically shaped recess surface is substantially perpendicular to the body egress and ingress surfaces.

6. The device of claim 1, wherein the recess surface reflectivity is greater than 99 percent.

7. The device of claim 1, wherein the profile shape of the input opening is configured to correspond to an emitting area of the solid state light source.

8. The device of claim 1, wherein the profile shape of the input opening is selected from the group consisting of circular, rectangular, and square.

9. A method for increasing the optical power of a solid state light source with a phosphor layer in the green and/or yellow bands for improved fluorescence microscopy comprising the steps of:
providing an integrating cone comprising an input opening, an output opening, and a reflective interior surface formed between the input opening the output opening;
receiving substantially blue light from a large area solid state lighting device into the input opening;
receiving substantially green and/or yellow light from the phosphor layer into the input opening;
emitting a first portion of received blue light directly through the output opening;
reflecting and scattering with the reflector interior surface a second portion of the received blue light back to the phosphor layer;
converting, with the phosphor layer, at least some of the second portion of the reflected and scattered blue light to green and/or yellow light; and
emitting the received and the converted green and/or yellow light through the output opening.

10. A system comprising:
a first solid state lighting device with a phosphor layer;
a first integrating cone comprising an input opening, an output opening, and a reflective interior surface formed between the input opening the output opening, the integrating cone configured to receive, integrate, and reshape light from the solid state lighting device and the phosphor layer through the interior surface and to emit light through the output opening;
a collecting lens configured to receive light emitted from the first integrating cone; and
a collimating lens configured to collimate light received from the collecting lens.

11. The system of claim 10, further comprising a microscopy system configured to receive collimated light from the collimating lens.

12. The system of claim 10, wherein the output opening has a smaller area than an area of the input opening.

13. The system of claim 10, wherein the reflective interior surface is configured to reflect visible light with Lambertian scatter characteristics.

14. The system of claim 10, further comprising;
a second large area solid state lighting device with a phosphor layer;
a second integrating cone comprising an input opening, an output opening, and a reflective interior surface formed between the input opening the output opening, the integrating cone configured to receive, integrate, and reshape light from the solid state lighting device and the phosphor layer through the interior surface and to emit light through the output opening; and
a combining device configured to blend light emitted from the first integrating cone and the second integrating cone and direct blended light to the collecting lens.

15. The system of claim 10, wherein the second large area solid state lighting device has different illumination characteristics from the first large area solid state lighting device.

16. The system of claim 15, wherein the second large area solid state lighting device produces a different range of wavelengths than the first large area solid state lighting device.

17. The system of claim 10, further comprising a light guide disposed between the cone and a target.

18. The system of claim 17, wherein the output of the light guide is collimated and coupled to a microscopy system via an adaptor.

19. The system of claim 10, further comprising;
a second solid state lighting device configured to produce UV light; and
a combining device configured to blend light emitted from the first integrating cone and the second solid state lighting device and direct blended light to the collecting lens.

20. The system of claim 19, further comprising a third solid state lighting device configured to produce a wavelength light different from the first and second solid state lighting devices.

21. The system of claim 20, wherein the combining device comprises a dichroic filter/plate.

* * * * *

UNITED STATES PATENT AND TRADEMARK OFFICE
CERTIFICATE OF CORRECTION

PATENT NO.        : 9,581,314 B2
APPLICATION NO.   : 14/691987
DATED             : February 28, 2017
INVENTOR(S)       : Yong Wang et al.

It is certified that error appears in the above-identified patent and that said Letters Patent is hereby corrected as shown below:

On the Title Page

At (73): Assignee's name is listed as "Excelites Canada, Inc.". Assignee's correct name is Excelitas Canada, Inc.

Also at (73): Assignee's city of residence is listed as "Voudreuil-Doxion". Assignee's correct city of residence is Vaudreuil-Dorion.

Signed and Sealed this
Eighteenth Day of April, 2017

Michelle K. Lee
*Director of the United States Patent and Trademark Office*